United States Patent [19]

Spohn

[11] Patent Number: 5,977,397
[45] Date of Patent: Nov. 2, 1999

[54] REMOVAL OF AN IMPURITY FROM A MIXTURE WITH A CODISTILLANT

[76] Inventor: Ronald Spohn, 112 Woodshire S., Getzville, N.Y. 14068

[21] Appl. No.: 09/291,457

[22] Filed: Apr. 14, 1999

[51] Int. Cl.$^6$ .................................................. C07C 255/00
[52] U.S. Cl. ............................................................ 558/425
[58] Field of Search ............................................. 558/425

[56] References Cited

U.S. PATENT DOCUMENTS 5,866,709  2/1999  Hausladen et al. ..................... 558/329

*Primary Examiner*—Johann Richter
*Assistant Examiner*—Joseph Murray
*Attorney, Agent, or Firm*—Anne E. Brookes; Richard D. Fuerle

[57] ABSTRACT

Disclosed is a method of removing an acid halide, anhydride, or ester impurity from a mixture with a desired product with which it codistills. At least about a stoichiometric amount of a primary or secondary amine having a boiling point at least 10° C. higher or lower than the boiling point of said desired product is added to the mixture. The desired product is not an acid halide, anhydride, or ester and does not react with the amine. The amine forms a reaction product with the impurity that has a boiling point at least 10° C. higher or lower than the boiling point of the desired product. The mixture is distilled to isolate the desired product.

20 Claims, No Drawings

REMOVAL OF AN IMPURITY FROM A MIXTURE WITH A CODISTILLANT

BACKGROUND OF THE INVENTION

This invention relates to a method of removing an acid halide, anhydride, or ester from a mixture with a compound with which it codistills. In particular, it relates to reacting the acid halide, anhydride, or ester with an amine to form a higher or lower boiling compound, followed by distillation.

Parachlorobenzonitrile (PCBN) can be used to make pigments, pharmaceuticals, and agricultural products. It is made by reacting parachlorobenzoic acid with parachlorobenzotrichloride (PCBTC) and ammonium chloride (see U.S. Pat. No. 5,866,709, herein incorporated by reference). In making PCBN, various side products and unreacted starting material can end up in the product mixture. Most of these impurities can be separated by distillation, but the boiling point of one side product, parachlorobenzoyl chloride (PCBOC), is only 2° C. less than the boiling point of PCBN(223° C.),so it codistills with the PCBN. The presence of PCBOC in the PCBN is not acceptable to some users of PCBN as it lowers the quality of the products made from PCBN. While separation could be accomplished by crystallation or further distillation, those processes are not cost effective.

SUMMARY OF THE INVENTION

I have discovered that an acid halide, anhydride, or ester impurity can be separated from a mixture with a compound with which they codistill by reacting the impurity with an amine to form a higher or lower boiling compound, then distilling. In particular, I have found that PCBOC can be separated from a mixture with PCBN by adding an amine, such as diphenyl amine (DPA), to the mixture to form a p-chlorobenzamide, such as N,N-diphenyl(p-chloro) benzamide (DPPCPA). I have further found that although one mole of hydrogen chloride is produced when one mole of PCBOC reacts with one mole of DPA, and one might expect that 2 moles of the amine would therefore be required (one to react with the PCBOC and one to react with the HCl), only one mole of amine is needed.

DESCRIPTION OF THE PREFERRED EMBODIMENTS

The process of this invention is applicable to any mixture of two compounds that codistill, where one of the compounds, the impurity, is an acid halide, an anhydride, or an ester and the other compound, the desired product, is not an acid halide, anhydride or ester and does not react with the amine used in the process. The impurity is preferably an acid halide and is most preferably an acid chloride as those impurities are of greater commercial importance. Examples of such mixtures include PCBOC in PCBN, 3,4-dichlorobenzoyl chloride in 3,4-dichlorobenzonitrile, o-chlorobenzoyl chloride in o-chlorobenzonitrile, acrylyl chloride in acrylonitrile, pivalyl chloride in pivalyl nitrile, dichloro acetyl chloride in dichloro acetyl nitrile, m-fluorobenzoyl chloride in m-fluorobenzonitrile, and benzoyl chloride in methyl benzoate. The invention is particularly useful in separating PCBOC from PCBN. While the invention can be used to remove any amount of the impurity from the desired product, it is less practical when the amount of impurity is less than about 0.1 wt % or is more than about 10 wt %; in the most practical range, the impurity is about 1 to about 3 wt % of the mixture.

Almost any primary or secondary amine, including diamines and polyamines, can be used to react with the impurity. The boiling point of the amine should be at least about 10° C. above or below the boiling point of the desired product, and preferably is at least about 20° C. above or below the boiling point of the product, so that any unreacted amine does not distill with the product. While lower-boiling amines can be used to react with the impurity to form a lower-boiling compound, it is preferable to use an amine with a higher boiling point than the product and thereby form a higher-boiling reaction product with the impurity, as that avoids handling another product. If a hydrogen halide byproduct, such as hydrogen chloride, is produced, the amine is preferably stable in it so that amine is not wasted reacting with it. Examples of amines that can be used include DPA, aniline, piperidine, diethanolamine, and N-benzyl-2-phenethylamine. The preferred amine is DPA because it can be easily melted to form a liquid (mp=54° C.), it is inexpensive, and its boiling point is 302° C., which is much higher than the boiling point of PCBN. The amount of amine used should be at least about stoichiometric with the amount of impurity. It is preferable to use a slight excess of amine (about 0.1 to about 0.3 equivalents per equivalent of impurity in excess of stoichiometric) to ensure that all of the impurity is reacted. The use of more than about 0.8 equivalents excess amine is unnecessary.

The amine is added to the mixture of the impurity and desired product and the mixture is heated to promote the reaction of the amine with the impurity and to distill off the desired product. While the heating can be to reflux, vacuum distillation can be used at a lower temperature. No catalyst or solvent is needed for this reaction.

The following examples further illustrated this invention:

EXAMPLE 1

To a sample of pure PCBN was added 2 wt % PCBOC followed by 1.1 eq. of DPA (Aldrich, reagent grade). The mixture was heated and sampled by gas chromatography (GC). Within 0.5 h at 150° C., no PCBOC was detected. Distillation through a 2 inch by 36 inch (5.1 by 91.4 cm) column packed with ¼ inch (0.6 cm) ceramic saddles produced PCBN free of PCBOC, DPA, and DPPCPA.

EXAMPLE 2

To 1573.6 g of lab-generated, up-and-over distilled PCBN (mp 95° C.) at 130° C. was added 30.21 g (173 mmoles) of PCBOC followed by 32.07 g, (190 mmoles, 1.1 eq) of melted DPA (mp 54° C.). The mixture was stirred at 130° C. and sampled by GC. After only 5 minutes, a sample showed that 83% of the PCBOC had been consumed. The mixture was stirred for another 30 min. at 130 to 150° C. and resampled; no PCBOC was detected. Distillation under vacuum afforded 2 clean cuts. The pot residue represented about 17% of the charge. The following table summarizes the GC analysis of the sequence. Values are GC area % on a DB-5 column.

| Sample | Description | PCBN | PCBOC | DPA | DPPCPA | Total |
|---|---|---|---|---|---|---|
| 1 | Pot after addition of 2 wt % PCBOC | 97.71 | 1.32 | 0.00 | 0.00 | 99.0 |
| 2 | Pot after addition of DPA at 130° C. | 93.60 | 0.22 | 2.68 | 1.46 | 98.0 |
| 3 | Pot 30 min. later | 93.20 | 0.00 | 1.12 | 4.69 | 99.0 |
| 4 | Cut 1 50 mm Hg vacuum | 99.50 | 0.00 | 0.00 | 0.00 | 99.5 |

-continued

| Sample | Description | PCBN | PCBOC | DPA | DPPCPA | Total |
|---|---|---|---|---|---|---|
| 5 | Cut 2 50 mm Hg vacuum | 99.53 | 0.00 | 0.00 | 0.00 | 99.5 |
| 6 | Bottoms | 70.81 | 0.00 | 4.44 | 20.17 | 95.4 |

EXAMPLE 3

To 75.8 g of PCBN containing 2 wt % PCBOC was added 4 wt % (3.0 g, 2.0 eq.) DPA. The mixture was stirred at 150° C. for 1.5 h and sampled by GC. No PCBOC was detected. A large excess of DPA was used to make sure all the PCBOC was consumed and to test the stability of both the DPA and the resultant DPPCPA to atmospheric up-and-over distillation temperatures. No problems were encountered with exotherms, bumping, etc., either during the hold at 150° C. or during the distillation with pot temperatures up to 235° C. at atmospheric pressure. The pot contents after the up-and-over distillation remained liquid at 100° C. and below. The up and over distillation afforded an 89.2% yield of isolated material. The GC analysis of this is given in the following table. Values are GC area % on a DB-5 column.

| Sample | Description | PCBN | PCBOC | DPA | DPPCPA | Total |
|---|---|---|---|---|---|---|
| 1 | PCBN with 2 wt % PCBOC | 97.51 | 1.41 | 0.00 | 0.00 | 98.9 |
| 2 | After addition of DPA | 91.17 | 0.86 | 5.18 | 1.09 | 98.3 |
| 3 | After stirring for 1.5 h | 90.35 | trace | 3.15 | 5.43 | 98.9 |
| 4 | Up & over | 98.62 | 0.00 | 0.56 | 0.07 | 99.3 |
| 5 | Pot bottoms | 37.65 | 0.00 | 16.83 | 42.06 | 96.5 |

Because the up-and-over column had at most only 1 plate, the purity of the product was slightly lower.

EXAMPLE 4

To 39.20 g of DCBN (dichlorobenzonitrile) was added 0.40 g DCBOC (dichlorobenzoylchloride, 1.91 mmoles). The mixture was sampled by GC and found to contain 0.57 GC area % DCBOC. To this mixture was added 0.40 g DPA (2.36 mmoles; 1.24 eq.). The mixture was stirred at 90° C. for 15 min and sampled. The GC area % of DCBOC was reduced to 0.45%. Heating was continued for an additional 45 min at 90° C. and the mixture was sampled again; only 0.06% DCBOC was detected.

We claim:

1. A method of removing an acid halide, anhydride, or ester impurity from a mixture with a desired product with which it codistills comprising
   (A) adding to said mixture at least about a stoichiometric amount of a primary or secondary amine having a boiling point at least 10° C. higher or lower than the boiling point of said desired product, where said desired product is not an acid halide, anhydride, or ester and does not react with said amine, whereby said amine forms a reaction product with said impurity that has a boiling point at least 10° C. higher or lower than the boiling point of said desired product; and
   (B) distilling said mixture.

2. A method according to claim 1 wherein said mixture is about 0.1 to about 10 wt % impurity and about 90 to about 99.9 wt % desired product.

3. A method according to claim 1 where said impurity is an acid chloride.

4. A method according to claim 3 wherein said impurity is parachlorobenzoyl chloride and said desired product is parachlorobenzonitrile.

5. A method according to claim 3 wherein said amine is stable in hydrogen chloride at the temperature that it reacts with said impurity.

6. A method according to claim 1 wherein said amine is diphenyl amine.

7. A method according to claim 1 wherein said amine has a higher boiling point than the boiling point of said desired product.

8. A method according to claim 1 where no solvent is present in said mixture.

9. A method according to claim 1 wherein no catalyst is present in said mixture.

10. A method according to claim 1 wherein the amount of said amine is about stoichiometric to about 0.8 equivalents in excess of stoichiometric.

11. A method according to claim 1 where said mixture is made by reacting parachlorobenzoic acid with benzoic acid and ammonium chloride.

12. A method of removing an acid chloride from a mixture with the corresponding nitrile comprising
   (A) adding to said mixture, in an amount about 0.1 to about 0.3 equivalents in excess of stoichiometric, a primary or secondary amine having a boiling point at least 20° C. higher than the boiling point of said nitrile, whereby said amine reacts with said acid chloride to form an amide and hydrogen chloride; and
   (A) heating said mixture to distill off said nitrite.

13. A method according to claim 12 wherein said amine is diphenyl amine.

14. A method according to claim 12 wherein said acid chloride is parachlorobenzoyl chloride and said desired product is parachlorobenzonitrile.

15. A method according to claim 12 wherein vacuum distillation is used in step (B).

16. A method according to claim 12 wherein said mixture is made by reacting parachlorobenzoic acid with parachlorobenzotrichloride and ammonium chloride.

17. A method of removing parachlorobenzoyl chloride from a mixture with parachlorobenzonitrile comprising
   (A) adding diphenyl amine to said mixture in an amount about 0.1 to about 0.3 equivalents in excess of stoichiometric, whereby said diphenyl amine reacts with said parachlorobenzoyl chloride to form N,N-diphenyl(p-chloro) benzamide; and
   (B) heating said mixture to a temperature sufficient to evaporate said parachlorobenzonitrile, but insufficient to evaporate said parachlorobenzoyl chloride, said diphenyl amine, or said N, N-diphenyl(p-chloro) benzamide.

18. A method according to claim 17 wherein said mixture is made by reacting parachlorobenzoic acid with parachlorobenzotrichloride and ammonium chloride.

19. A method according to claim 16 wherein no solvent is present in said mixture.

20. A method according to claim 16 wherein no catalyst is present in said mixture.

* * * * *